(12) United States Patent
Flandrois et al.

(10) Patent No.: US 8,756,026 B2
(45) Date of Patent: Jun. 17, 2014

(54) MONITORING PARTICLES IN A LUBRICATION SYSTEM

(75) Inventors: Xavier Flandrois, Cesson (FR); Jean-Rémi André Masse, Saint Cloud (FR); Maurice Georges Vernochet, La Rochette (FR)

(73) Assignee: SNECMA, Paris (FR)

( * ) Notice: Subject to any disclaimer, the term of this patent is extended or adjusted under 35 U.S.C. 154(b) by 379 days.

(21) Appl. No.: 13/210,012

(22) Filed: Aug. 15, 2011

(65) Prior Publication Data

US 2012/0046896 A1 Feb. 23, 2012

(30) Foreign Application Priority Data

Aug. 17, 2010 (FR) .................................... 10 56632

(51) Int. Cl.
*G06F 19/00* (2011.01)
*G01R 27/00* (2006.01)
*F16N 29/00* (2006.01)
*G01N 33/28* (2006.01)
*G01N 27/10* (2006.01)

(52) U.S. Cl.
CPC ............ *F16N 29/00* (2013.01); *G01N 33/2888* (2013.01); *G01N 27/10* (2013.01); *F16N 2200/04* (2013.01); *F16N 2200/14* (2013.01)
USPC .............................. 702/65; 73/53.01; 702/149

(58) Field of Classification Search
CPC . F16N 29/00; F16N 2200/04; F16N 2200/14; F16N 2250/30; F16N 2250/36; F16N 2260/18; G01N 33/2888; G01N 27/10; G01N 2035/1062; G01N 33/2876; F01M 2011/14; F01M 2011/1406; F01M 2011/1413; F01M 2011/1453; F01M 2011/1466; F01M 2011/148

USPC ............ 702/38, 44, 57, 65, 72, 80, 105, 115, 702/149; 73/53.01, 54.01, 61.61; 324/698
See application file for complete search history.

(56) References Cited

U.S. PATENT DOCUMENTS

| 5,027,065 A | 6/1991 | Bares et al. |
| 7,581,434 B1 | 9/2009 | Discenzo et al. |

FOREIGN PATENT DOCUMENTS

| EP | 0 398 800 A1 | 11/1990 |
| FR | 2 939 928 A1 | 6/2010 |
| WO | WO 2006/066714 A1 * | 6/2006 |

OTHER PUBLICATIONS

French Preliminary Search Report issued Mar. 30, 2011, in French 1056632, filed Aug. 17, 2010 (with English Translation of Category of Cited Documents).

(Continued)

*Primary Examiner* — John H Le
(74) *Attorney, Agent, or Firm* — Oblon, Spivak, McClelland, Maier & Neustadt, L.L.P.

(57) ABSTRACT

A process for monitoring a machine including moving pieces, a lubrication system and an electromagnetic sensor fitted with a magnet and two electrodes is disclosed. The sensor is capable of collecting particles present in the lubrication system between the electrodes. The monitoring process includes a step for obtaining measurements of resistance between the electrodes of the sensor, taken during an operating period of the machine; a step for determining from said measurements a first autoregressive mathematical model characterizing the resistance; a step for comparison between the first model and a predetermined reference model; and a step for working out an opinion on maintenance of the machine as a function of the comparison result.

12 Claims, 1 Drawing Sheet

(56) References Cited

OTHER PUBLICATIONS

Qiang Wang, et al., "Engine Condition Monitoring Based on Grey AR Combination Model", International Conference on Challenges in Environmental Science and Computer Engineering, Mar. 6, 2010, XP031695449, pp. 215-218.

* cited by examiner

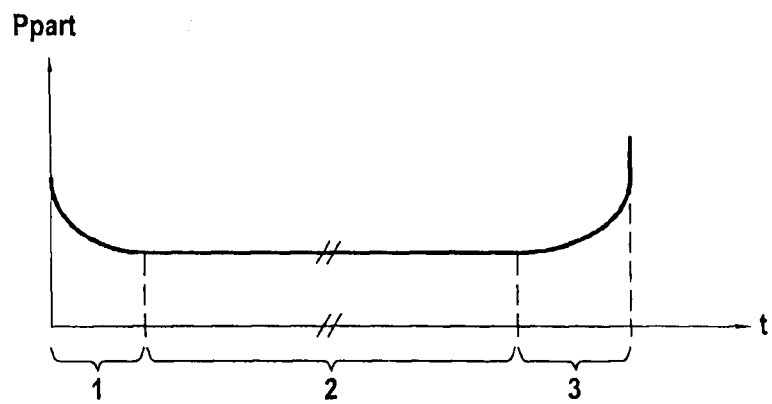
FIG.1
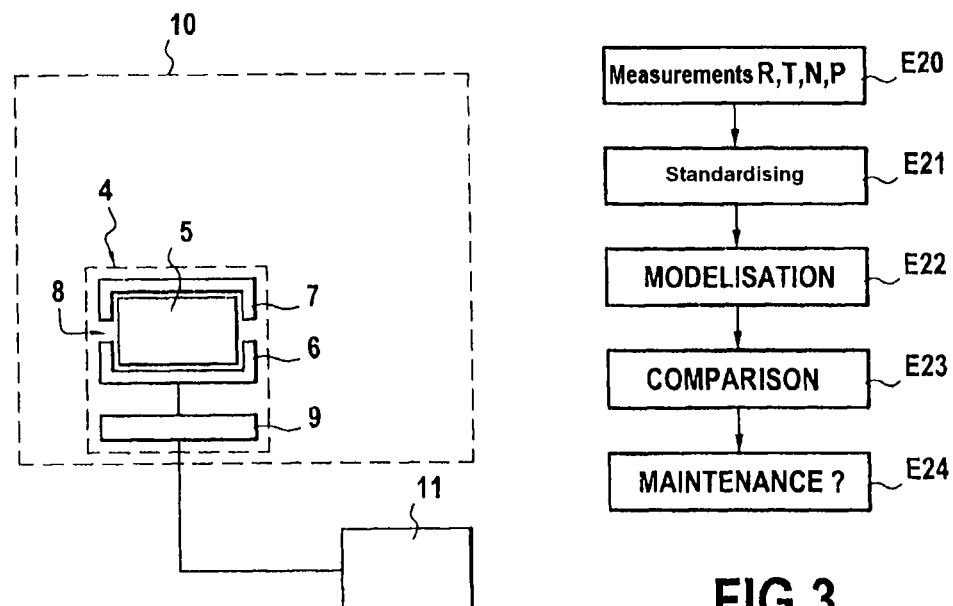
FIG.2
FIG.3

MONITORING PARTICLES IN A LUBRICATION SYSTEM

BACKGROUND OF THE INVENTION

The present invention relates to the general field of aeronautics.

It concerns more particularly the monitoring of an aircraft engine, equipped with a sensor designed to hold back metallic particles taken in by the lubricating oil of the engine resulting from wearing of moving pieces.

As is known, the moving pieces of an aircraft engine, such as gears or bearings, are subjected to wearing phenomena such as scaling. These wearing phenomena are evident especially in the appearance of particles of a more or less large size in the lubrication circuit of the engine. These particles play a major role in detecting and providing engine breakdown.

In fact, as shown in the graph of FIG. 1, the production of particles $P_{part}$ in an engine comprising moving pieces evolves over time t. More precisely, during a phase 1 of running-in, the production rate of particles is relatively high and decreases progressively. The running-in phase 1 is followed by a normal use phase 2, during which production of particles stabilises. Finally, during a terminal wear phase 3, wear on more loaded pieces involving a higher particle production rate, including bursting if no maintenance is done.

The use of sensors (or detectors) of particles in the lubrication system of the engine therefore monitors the presence of these particles, and even the status of the engine. Preventive maintenance on the engine is then feasible, especially when large-size particles are detected in an abnormal quantity, which might anticipate an engine breakdown.

An example of such a sensor is an electromagnetic plug, also known by the name "Electric Chip Detector" (ECD) or "Electro Magnetic Chip Detector" (EMCD) in English, located in the lubrication system of the engine upstream of the filters. Such a plug advantageously detects, simply and automatically, without need for visual monitoring, the metallic particles carried along in the engine oil. The invention preferably applies to this type of sensor.

As is known, an electromagnetic plug is equipped with a magnet surrounded by two conductive electrodes insulated from each other, and separated by a gap integrated in an electric circuit. When a large quantity of metallic particles circulates in the lubrication system, the latter are captured by the magnet and shunt (i.e. short-circuit) the gap of the electromagnetic plug, making contact between the two electrodes. The resulting contact causes a drop in resistance measured between the electrodes.

A processing circuit linked to the plug and integrated for example in the engine controller (or FADEC, Full Authority Digital Engine Control), compares the measured resistance between the electrodes of the plug to a threshold value and when this threshold value is exceeded generates a warning message for an engine maintenance system or for the pilot of the aircraft. When this message is received, the plug can then be disassembled for more advanced analysis of the state of the particles or for maintenance work.

Such functioning advantageously avoids periodic control of the particle sensor, and especially disassembly of the latter in the absence of a warning message. However, the threshold value of the resistance from which a warning message is generated is difficult to determine, the latter depending on several parameters including especially engine type, application, engine age, environmental context, etc.

In this way, for safety reasons, there is a tendency to consider a sufficiently high threshold value so as not to neglect a critical engine wear situation. However, the flip side to using a high threshold value is a high rate of false alarms, limiting the impact of such a plug.

There is therefore a need for process and a monitoring device which does not have these disadvantages and uses electromagnetic plugs currently deployed on numerous aircraft.

AIM AND SUMMARY OF THE INVENTION

The present invention responds to this need especially by proposing a monitoring process for a machine comprising moving pieces, a lubrication system and an electromagnetic sensor fitted with a magnet and two electrodes, said sensor being capable of collecting particles present in the lubrication system between said electrodes, the monitoring process comprising a step for obtaining measurements of resistance between the sensor electrodes, taken during a period when the machine is running, the monitoring process being characterised in that it comprises;

a step for determining, from said measurements, a first autoregressive mathematical model characterising said resistance;

a comparison step between the first model and a predetermined reference model; and a step for developing an opinion on maintenance of the machine as a function of the comparison result.

The inventors have noted that during the normal use phase of a machine the measured resistance was stationary in statistical and spectral terms. On the contrary, the start of the terminal wear phase can be characterised by a change in spectral characteristics. Comparison of the first mathematical model with the reference model shows a change in the spectral characteristics and therefore reliably detects the start of the terminal wear phase. In this way, the invention prevents or limits false alarms.

According to an embodiment, the comparison step comprises evaluation of a distance between the first model and the reference model and said developing step provides a positive opinion on maintenance if this distance is greater than a predefined threshold.

The monitoring process can comprise, prior to the determining step, a step for standardising the measurements relative to at least one of the following environmental variables:
temperature of the lubrication system;
pressure of the lubrication system; and
machine speed.

As a variant, the first model and the reference model are ARX models, given at least one of the following exogenic variables:
temperature of the lubrication system;
pressure of the lubrication system; and
machine speed.

The distance between the first model and the reference model can be a Euclidian distance calculated between the coefficients of the first model and the coefficients of the reference model, or a Euclidian distance calculated between the poles of the first model and the poles of the reference model.

The distance between the first model and the reference model can also be a Euclidian distance calculated between the residues of the first model and the residues of the reference model.

According to a variant, the monitoring process comprises a plurality of executions of the determining step to determine a plurality of autoregressive models for a plurality of operating periods of the machine, and the step for developing comprises working out an opinion on positive maintenance of the sensor if the Euclidian distance calculated between each autoregressive model and the reference model increases during successive operating periods of the machine.

According to an embodiment, said machine is an aircraft engine and the measurements of resistance between the electrodes of the sensor are made during a flight phase of the aircraft.

The invention also provides a monitoring device of a machine comprising moving pieces, a lubrication system and an electromagnetic sensor fitted with a magnet and two electrodes, said sensor being capable of collecting particles present in the lubrication system between said electrodes, the monitoring device comprising means for producing measurements of resistance between the electrodes of the sensor, made during an operating period of the machine, the monitoring device being characterised in that it comprises;

means for determining, from said measurements, a first autoregressive mathematical model characterising said resistance;

comparison means between the first model and a predetermined reference model; and means for working out an opinion on maintenance of the machine as a function of the comparison result.

The invention also proposes an aircraft engine comprising moving pieces, a lubrication system, an electromagnetic sensor fitted with a magnet and two electrodes, said sensor being capable of collecting particles present in the lubrication system between said electrodes, and a monitoring device according to the invention.

In a particular embodiment, the different steps of the monitoring process are determined by computer program instructions.

As a consequence, the invention also provides a computer program on a data medium, this program being capable of being run in a monitoring device or more generally in a computer, this program comprising instructions adapted to conducting steps of a monitoring process such as described hereinabove.

This program can use any programming language, and be in the form of source code, target code, or intermediate code between source code and target code, such as in a partially compiled form, or in any other preferred form.

The invention also provides a data medium readable by a computer and comprising computer program instructions such as mentioned hereinabove.

The data medium can be any entity or device capable of storing the program. For example, the support can comprise storage means, such as ROM, for example a CD ROM or microelectronic circuit ROM, or even magnetic recording means, for example a diskette (floppy disc) or hard drive.

On the other hand, the data medium can be a transmissible medium such as an electric or optic signal, which can be sent via an electric or optic cable, by radio or by other means. The program according to the invention can be downloaded in particular from a network of Internet type.

Alternatively, the data medium can be an integrated circuit incorporating the program, the circuit being adapted for executing or to be used in executing the process in question.

BRIEF DESCRIPTION OF THE DIAGRAMS

Other characteristics and advantages of the present invention will emerge from the following description, in reference to the attached diagrams which illustrate an embodiment devoid of any limiting character. In the figures;

FIG. 1 is a graph illustrating evolution of the production of particles in a machine comprising moving pieces, FIG. 2 schematically illustrates an example of an electromagnetic plug in its environment, and FIG. 3 illustrates the principal steps of a monitoring process according to an embodiment of the invention.

DETAILED DESCRIPTION OF AN EMBODIMENT

FIG. 2 schematically illustrates an electromagnetic plug 4 integrated in the lubrication system 10 of an aircraft engine turbomachine. The electromagnetic plug 4 comprises a magnet 5 surrounded by two conductive electrodes 6 and 7 insulated from each other, and separated by a gap 8 integrated in an electric circuit. When a large quantity of metallic particles circulates in the lubrication system 10, the latter are captured by the magnet 5 and shunt (i.e. short-circuit) the gap 8, making contact between the electrodes 6 and 7. The resulting contact cause a drop in resistance measured between the electrodes 6 and 7. Other configurations of the magnet and electrodes are possible.

The electromagnetic plug 4 comprises an interface 9 linked to an electronic unit 11, which allows the electronic unit 11 to obtain a measurement signal representing resistance between the electrodes 6 and 7. The electronic unit 11 is for example the controller of the engine (or FADEC, Full Authority Digital Engine Control) or a unit specific to monitoring the engine.

The electronic unit 11 runs a monitoring process of the engine, and as a function of measurements of resistance between the electrodes 6 and 7 can generate an alarm message. When this alarm message is received, a maintenance operation can then be carried out.

The electronic unit 11 has the material architecture of a computer. It comprises especially a processor, read-only memory and read-write memory. The read-only memory stores a computer program comprising instructions for execution of the steps of a monitoring process according to the invention. The electronic unit 11 constitutes a monitoring device in terms of the invention, and its read-only memory constitutes an information medium in terms of the invention.

FIG. 3 illustrates the principal steps of the monitoring process carried out by the electronic unit 11.

When the electronic unit 11 detects a flight phase of the aircraft, execution of the process starts by way of step E20 during which the electronic unit 11 obtains and stores measurements of resistance R between the electrodes 6 and 7, as well as measurements of speed N of the turbomachine, temperature T and pressure P of the lubrication system oil 10. In this way, the electronic unit 11 acquires values representing time evolutions of resistance $R(t)$, speed $N(t)$, temperature $T(t)$ and pressure $P(t)$, during a flight phase of the aircraft.

In a variant, not shown, step E20 is followed by a step for validation of data. In the event of invalid data, the following steps E21 to E24 are not executed. This does not work out an opinion on maintenance based on invalid data, for example due to a defective sensor.

Step E21 is a step for standardising data. More precisely, the measured resistance $R(t)$ is standardised to take into account the context of the measurements. In this way, standardised resistance $R_{norm}(t)$ is determined as a function of the resistance $R(t)$ and parameters of context which can influence the resistance not representative of particle production. The parameters of context used are speed $N(t)$, temperature $T(t)$ and pressure $P(t)$. Standardising can for example be done according to the technique described in document FR 2 939 928.

Next, in step E22, an autoregressive mathematical model characterising standardised resistance is determined. More precisely, a model AR (Auto Regressive model) is determined for predicting resistance $R_{norm}(t)$:

$$R_{norm}(t) = \sum_{j=1}^{J} a_j \cdot R_{norm}(t-j) + \eta(t)$$

where $a_j$ are the coefficients of the model AR and $\eta(t)$ is white noise. Determining the mathematical model consists of determining the coefficients $a_j$ as a function of standardised resistance $R_{norm}(t)$ determined in step E21, according to known modelling techniques.

In a variant not shown here, the process omits the standardisation step E21. In this case, the autoregressive mathematical model used is a model ARX (Auto Regressive model with eXternal inputs) in which the exogenic variables used are speed $N(t)$, temperature $T(t)$ and pressure $P(t)$. In this variant, the model can be expressed as follows:

$$R(t) = \sum_{j=1}^{J} a_j \cdot R(t-j) + \sum_{k=1}^{K} b_k \cdot N(t-k) + \sum_{l=1}^{L} c_l \cdot T(t-l) + \sum_{m=1}^{M} d_m \cdot P(t-m) + \eta(t)$$

Where $a_j$, $b_k$, $c_l$ and $d_m$ are the coefficients of the model ARX.

As is known, the models AR and ARX can also be expressed by a transform in Z, characterised by its poles. As is also known, the residues of a model illustrate the differences between the measured values and the values predicted by the model.

The model determined in step E22 is compared in step E23 to a predetermined reference model and in step E24 an opinion on maintenance of the aircraft engine is worked out as a function of the comparison result.

During normal use phase 2 of the turbomachine, the measured resistance is variable during flight and from one flight to the other, especially due to the discontinuous character of the circulation of particles in the lubrication system 10. In this way, as explained in the introduction, comparison of resistance R measured with a predetermined threshold does not provide reliable detection of the start of terminal wear phase 3.

The inventors have noticed however that during phase 2 resistance R was stationary in statistical and spectral terms once standardised. On the contrary, the start of phase 3 can be characterised by a change in spectral characteristics.

In this way, comparison of the model determined in step E22 with a reference model representative of the performance of resistance R during normal use phase 2 works out an opinion on engine maintenance. More precisely, if the comparison indicates a substantial difference between the models, a positive opinion on maintenance is worked out.

During comparison step E23, the difference between the models is evaluated by calculating a distance between the models.

According to a first variant, the distance is a Euclidian distance calculated between the coefficients of the first model and the coefficients of the reference model, or a Euclidian distance calculated between the poles of the first model and the poles of the reference model. In fact, the coefficients and the poles of an autoregressive mathematical model are representative of the spectral performance of the modelled variable. A big distance between the two models corresponds to a difference in spectral performance.

So in this first variant, during step E24 the electronic unit 11 estimates that phase 3 started when the distance between the model determined at step E23 and the reference model is greater than a predetermined threshold. In this case, a positive opinion on maintenance is worked out.

In another variant, the electronic unit 11 stores a plurality of models determined for a plurality of executions of step E23 during successive missions of the aircraft. For each stored model a Euclidian distance is calculated between the residues of the stored model and the residues of the reference model.

Next, during step E24 an opinion on positive maintenance is worked out if the distance between each autoregressive model and the reference model increases during successive missions of the aircraft. In fact, at the start of phase 3, modification of the spectral performance occurs via progressive increase of the residues from one flight to the other.

The reference model used during comparison step E23 is for example a predetermined model common to all engines of the same type, and saved in read-only memory of the electronic unit 11.

As a variant, the reference model is specific to each engine and is predetermined by the electronic unit 11 during a learning phase which precedes executing the process of FIG. 3. The learning phase is conducted at the start of phase 2. The start of phase 2 can be estimated using a safety margin as a function of average duration of phase 1. The reference model can then be determined as a function of the measurements of resistance R during several flights made at the start of phase 2.

The invention has been described in reference to monitoring a turbomachine of an aircraft engine. But the invention is generally applicable to any type of machine comprising moving pieces and a lubrication system.

Also, it is evident that the monitoring process can be carried out by using an electromagnetic plug of the prior art. The invention needs no modification of the plug or of its interface with the electronic control unit.

The invention claimed is:

1. A monitoring process of a machine comprising moving pieces, a lubrication system and an electromagnetic sensor fitted with a magnet and two electrodes, said sensor being capable of collecting particles present in the lubrication system between said electrodes, the monitoring process comprising:

acquiring, using a processor of a computer, measurements of resistance between the electrodes of the sensor, made during an operating period of the machine;

determining, using the processor of the computer, from said measurements a first autoregressive mathematical model characterizing said resistance;

comparing, using the processor of the computer, the first model and a predetermined reference model of resistance during a normal use phase of the machine, the reference model being stored in a memory of the computer, and the comparing comprising calculating a Euclidean distance between the first model and the reference model; and forming an opinion on maintenance of the machine as a function of the comparison result using the processor of the computer, in which a positive opinion on maintenance is provided if said Euclidean distance is greater than a predefined threshold.

2. The process of monitoring as claimed in claim 1, further comprising prior to said determining, standardizing measurements relative to at least one of the following environmental variables:
- temperature of the lubrication system;
- pressure of the lubrication system; or
- speed of the machine.

3. The process of monitoring as claimed in claim 1, wherein the first model and the reference model are models ARX taking into account at least one of the following exogenic variables:
- temperature of the lubrication system;
- pressure of the lubrication system; or
- speed of the machine.

4. The process of monitoring as claimed in claim 1, wherein the Euclidean distance between the first model and the reference model is calculated between the coefficients of the first model and the coefficients of the reference model.

5. The process of monitoring as claimed in claim 1, wherein the Euclidean distance between the first model and the reference model is calculated between the poles of the first model and the poles of the reference model.

6. The process of monitoring as claimed in claim 1, wherein the Euclidean distance between the first model and the reference model is calculated between the residues of the first model and the residues of the reference model.

7. The process of monitoring as claimed in claim 6, comprising a plurality of executions of said determining to determine a plurality of autoregressive models for a plurality of operating periods of the machine, wherein said forming includes forming an opinion on positive maintenance of the sensor if the Euclidian distance calculated between each autoregressive model and the reference model increases during successive operating periods of the machine.

8. The process of monitoring as claimed in claim 1, wherein said machine is an aircraft engine and the measurements of resistance between the electrodes of the sensor are made during a flight phase of the aircraft.

9. A computer program comprising instructions for executing the steps of the monitoring process, as claimed in claim 1 when said program is run on a computer.

10. A recording medium readable by computer which records a computer program comprising instructions for executing the steps of the monitoring process as claimed in claim 1.

11. A monitoring device of a machine comprising moving pieces, a lubrication system and an electromagnetic sensor fitted with a magnet and two electrodes, said sensor being capable of collecting particles present in the lubrication system between said electrodes, the monitoring device comprising:
- means for producing measurements of resistance between the electrodes of the sensor, taken during an operating period of the machine;
- means for determining from said measurements a first autoregressive mathematical model characterizing said resistance;
- comparison means for comparing the first model and a predetermined reference model of resistance during a normal use phase of the machine, the means for comparing comprising means for calculating a Euclidean distance between the first model and the reference model; and
- means for working out an opinion on maintenance of the machine as a function of the comparison result, in which a positive opinion on maintenance is provided if said Euclidean distance is greater than a predefined threshold.

12. An aircraft engine comprising moving pieces, a lubrication system, an electromagnetic sensor fitted with a magnet surrounded by two electrodes, said sensor being capable of collecting particles present in the lubrication system between said electrodes, and a monitoring device as claimed in claim 11.

* * * * *